United States Patent
Shah et al.

(10) Patent No.: US 8,166,832 B2
(45) Date of Patent: May 1, 2012

(54) OIL SAMPLING DEVICE HAVING A FLEXIBLE PISTON AND CHAMBER

(75) Inventors: Vatsal Mukundlal Shah, Sugar Land, TX (US); Priestley Jing-kong Wang, Houston, TX (US)

(73) Assignee: Shell Oil Company, Houston, TX (US)

( * ) Notice: Subject to any disclaimer, the term of this patent is extended or adjusted under 35 U.S.C. 154(b) by 525 days.

(21) Appl. No.: 12/519,931

(22) PCT Filed: Dec. 19, 2007

(86) PCT No.: PCT/US2007/088081
§ 371 (c)(1),
(2), (4) Date: Jun. 18, 2009

(87) PCT Pub. No.: WO2008/079860
PCT Pub. Date: Jul. 3, 2008

(65) Prior Publication Data
US 2010/0051125 A1 Mar. 4, 2010

Related U.S. Application Data

(60) Provisional application No. 60/871,358, filed on Dec. 21, 2006.

(51) Int. Cl.
*G01N 1/00* (2006.01)
*G01N 1/12* (2006.01)

(52) U.S. Cl. .................. 73/864.73; 73/864.62
(58) Field of Classification Search ............. 73/864.73, 73/864.62; 222/149, 416
See application file for complete search history.

(56) References Cited

U.S. PATENT DOCUMENTS

| | | | | |
|---|---|---|---|---|
| 2,057,398 A | | 10/1936 | Sperling | 137/18 |
| 3,958,589 A | * | 5/1976 | Geist et al. | 137/149 |
| 4,046,291 A | * | 9/1977 | Goda | 222/309 |
| 4,276,878 A | | 7/1981 | Storz | 128/218 |
| 4,548,088 A | | 10/1985 | Hood, Jr. | 73/864.34 |
| 4,925,627 A | | 5/1990 | Johnson | 422/99 |

FOREIGN PATENT DOCUMENTS

| | | |
|---|---|---|
| FR | 2628006 | 9/1989 |
| GB | 2283692 | 5/1995 |
| WO | WO03009884 | 2/2003 |
| WO | WO2004056411 | 7/2004 |

* cited by examiner

*Primary Examiner* — Hezron E Williams
*Assistant Examiner* — Nathaniel Kolb

(57) ABSTRACT

A device, system, and method for retrieving a sample of oil from an engine, comprising, a chamber having an inside wall and at least one oil inlet, a piston head received in said chamber and slidable between an empty position in which it is disposed substantially at said inlet and a filled position in which it is a first distance from said inlet, a handle affixed to said chamber, and a piston member extending between said handle and said piston head, said piston member comprising a flexible member having a proximal end and a distal end, said distal end being affixed to said piston head.

8 Claims, 4 Drawing Sheets

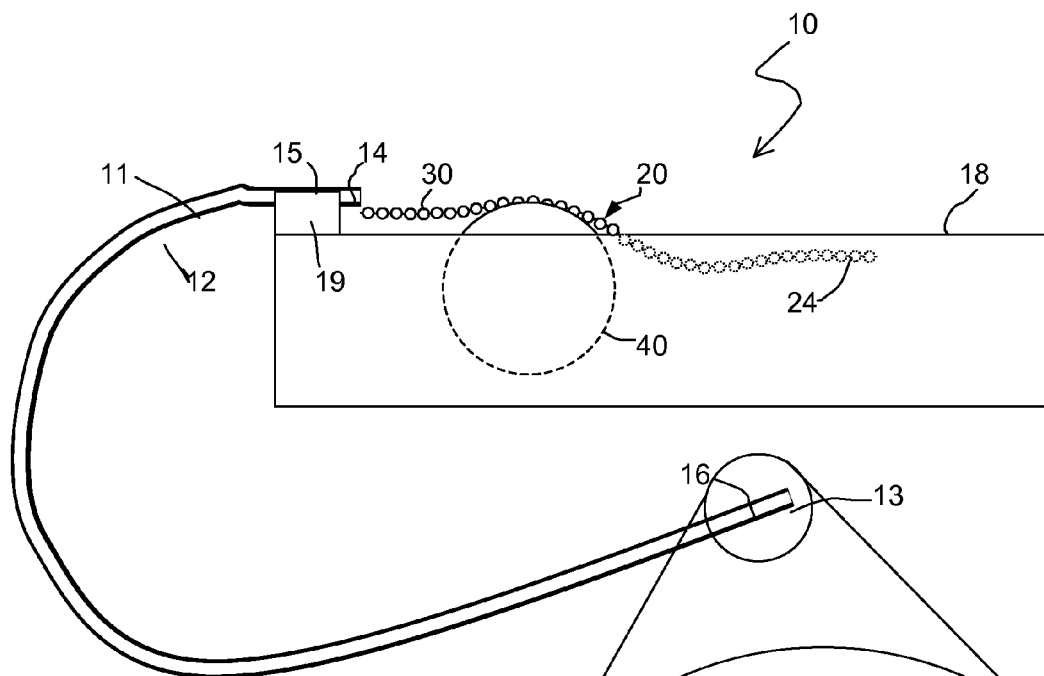
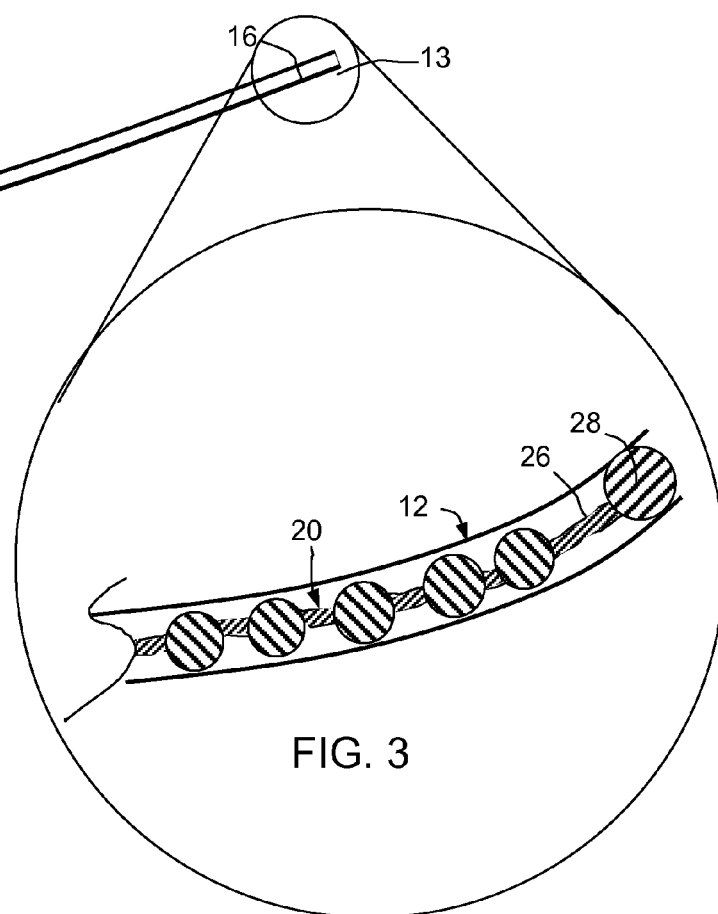
FIG. 2
FIG. 3

OIL SAMPLING DEVICE HAVING A FLEXIBLE PISTON AND CHAMBER

PRIORITY CLAIM

The present application claims priority from PCT/US2007/088081, filed 19 Dec. 2007, which claims priority from U.S. Provisional Application 60/871,358, filed 21 Dec. 2006.

FIELD OF INVENTION

The invention generally relates to a device and method for extracting a fluid sample from a reservoir that is relatively difficult to reach. More particularly, the present invention relates to a device and method for extracting a sample of motor oil from an engine.

BACKGROUND OF THE INVENTION

It is well known in the motor vehicle arts that the rate of mechanical wear on the engine depends in part on the lubricating ability of the oil that is used to lubricate the engine parts, (sometimes referred to as "engine oil" or "motor oil"). The lubricating ability of these oils degrades as the engine is operated over time. In order to prevent catastrophic failures, there are various tests and guidelines for determining when an engine oil should be changed. Because of the range of conditions under which an engine may be operated, however, it is more reliable to test the oil in question than to rely solely on guidelines to determine when an oil should be changed.

The quality of an oil sample taken from the engine indicates whether the oil has degraded beyond suitability for continued use. Various methods for assessing the quality of an oil sample have been standardized and are known. It is common to obtain an oil sample from the oil pan of the engine after the engine has been running, so that the assessment is performed on a sample that is representative of the overall oil quality. Because the oil pan is beneath the engine block, however, it is not readily accessed.

Currently, oil samples are obtained using a variety of techniques and devices. Some devices obtain fluid through the drain opening. These devices rely on gravity flow, but require access to the underside of the engine, which is relatively difficult.

Other devices obtain fluid through the dipstick tube, which does not require access to the underside of the engine. Because they cannot rely on gravity flow, however, these devices require means for drawing the oil up out of the oil reservoir. This may take the form of a reversible plunger mechanism, such as in the device shown in FIG. 1. In the device shown in FIG. 1, a rigid plunger is manually retracted using a finger loop, which in turn draws oil into an opening at the remote end of an oil sampling tube, as indicated by the arrows. When the desired amount of oil has been withdrawn, it is released into a sample collector (not shown) by using a spring-loaded ratchet mechanism to return the plunger to its original position. Because the sampling tube must fit within the dipstick opening, its inside diameter is relatively small. This means that, depending on the required sample size, the distance through which the plunger must be withdrawn can be relatively great.

Because of shortcomings with the afore-mentioned device, the available technology for obtaining an oil sample remains less than satisfactory. In some devices, such a those that use spring-loaded suction for withdrawing oil from the oil plan, the oil discharge mechanism may leave some oil clinging to the inside of the sample tube. This can contaminate the subsequent sample, resulting in a false reading or analysis. In addition, the combined length of the plunger, handle, and sample tube can be well over four feet, making the device difficult to handle. Still further, the plunger, when it has been retracted, is susceptible to buckling when force is applied to return it to its starting position. Thus, there is a need for a sampling device that avoids cross-contamination of samples and is compact and easy to use.

SUMMARY OF THE INVENTION

The present invention provides a device for retrieving a sample of oil from an engine. The device avoids cross-contamination of successive samples and is compact and easy to use. In some embodiments, the present device comprises a chamber having an inside wall and at least one oil inlet, a piston head slidably received in the chamber, a handle affixed to the chamber, and a piston member extending between the handle and the piston head, the piston member comprising a flexible member having a proximal end and a distal end, the distal end being affixed to the piston head.

In preferred embodiments, the chamber comprises a length of flexible tubing. In some embodiments, the tubing is preferably semi-rigid tubing such as PFA and FEP or other materials that are chemically inert and can be used at high operation temperatures without deforming. In addition, PFA, FEP and other fluorated plastics provide the desirable self-lubrication properties. The handle may include a thumbwheel that engages the piston member such that rotation of the thumbwheel advances or retracts the piston-advancing mechanism. In some embodiments, the piston member includes at least one engagement device and in certain embodiments may comprise a length of beaded cable tie.

The piston is preferably configured so as to move between an empty position in which said piston is at said oil inlet and a full position in which said piston is retracted from said oil inlet by a desired amount.

Any engines use lubricant oil to maintain their sustained operation for long time. The engines can be powered by gasoline, diesel, electric current, hydraulic, pneumatic or stream. In addition to motor oil, the present device also can be used to extract fluid samples from other places that are relatively difficult to access. The compact storage size of the present invention is another advantage over previous devices.

BRIEF DESCRIPTION OF THE DRAWINGS

Advantages of the present invention will become apparent to those skilled in the art with the benefit of the following detailed description of embodiments and upon reference to the accompanying drawings, in which:

FIG. 2 is a diagram of a device constructed in accordance with a first embodiment of the invention;

FIG. 3 is an enlarged cross-section of one portion of the embodiment of FIG. 2.

Figure 1:
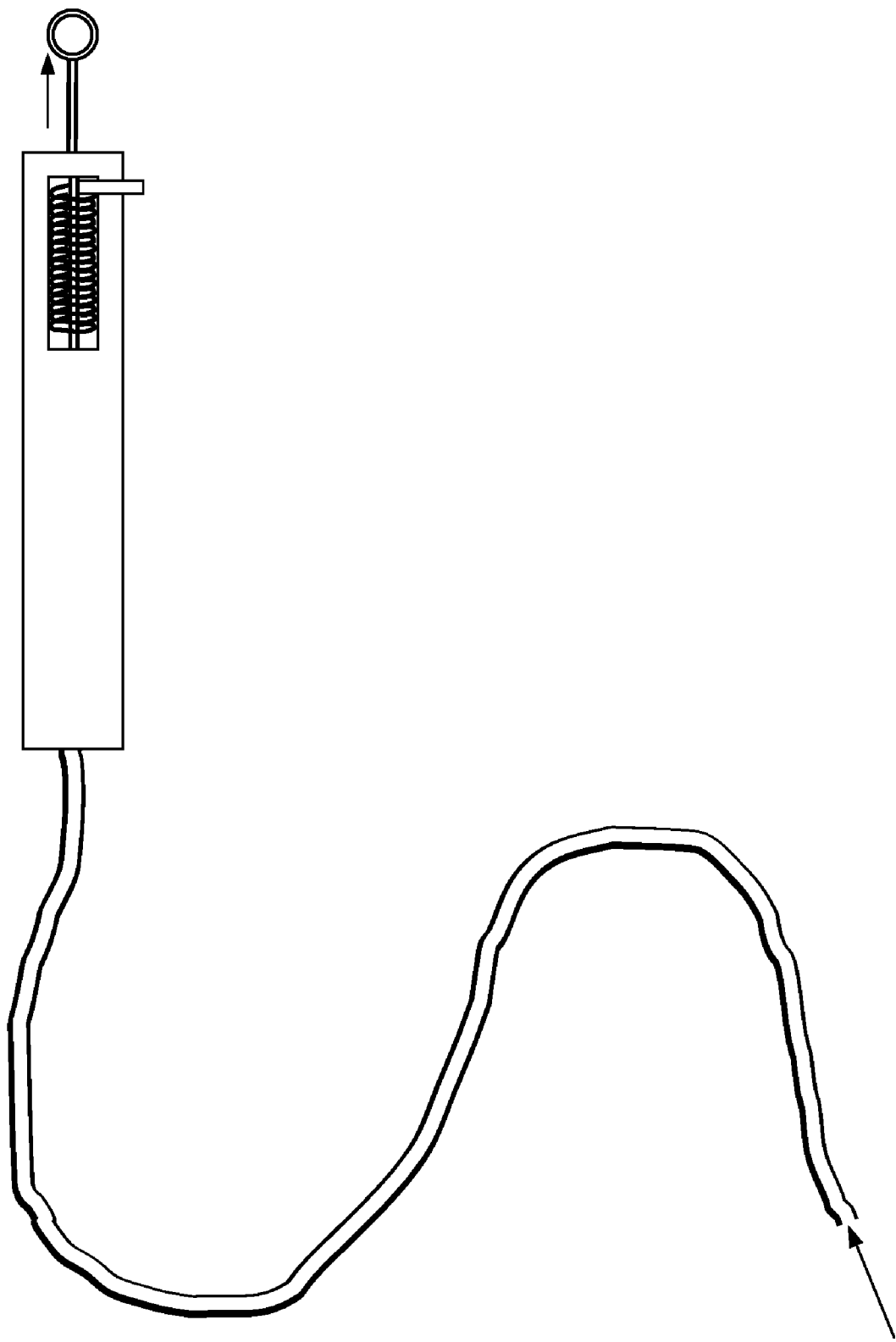
FIG. 1 is a diagram of a known oil extraction device.

While the invention is susceptible to various modifications and alternative forms, specific embodiments thereof are shown by way of example in the drawings and will herein be described in detail. It should be understood that the drawings and detailed description thereto are not intended to limit the invention to the particular form disclosed, but on the contrary, the intention is to cover all modifications, equivalents, and alternatives falling within the scope of the present invention as defined by the appended claims.

DETAILED DESCRIPTION OF THE INVENTION

Referring now to FIGS. 2 and 3, an oil extractor 10 constructed in accordance with a first embodiment of the invention includes a chamber 12 having a proximal end 14 and a distal end 16, a handle 18 affixed to the proximal end of chamber 12, and a piston member 20 slidably disposed within chamber 12. Chamber 12 includes an oil inlet 13. In certain embodiments, chamber 12 comprises a length of flexible tubing 11, and in particular embodiments may be constructed of a flexible, heat-resistant, transparent or translucent plastic.

Chamber 12 may be attached to handle 18 by any suitable means, such as a mounting clip 15. Mounting clip 15 may comprise a body 19 having a bore 17 (FIG. 4) therethrough. Proximal end 14 of chamber 12 may be disposed in bore 17 and affixed thereto, such as by adhesive or other means. Alternatively, proximal end 14 may be affixed to the outside of body 19, or directly to handle 18, if desired.

Piston member 20 is slidably disposed in chamber 12. Like chamber 12, piston member 20 has a proximal end 24 and a distal end 26 (FIG. 3). Distal end 26 includes a piston head 28 that is preferably sized to fit sealingly within chamber 12. Specifically, piston head 28 preferably fits sufficiently snugly that a fluid seal is formed between piston head 28 and the inside wall of chamber 12. In some embodiments, piston head 28 may be formed from or integrally with piston member 20. In alternative embodiments, piston head 28 may be formed separately and affixed to piston member 20.

Figure 5:
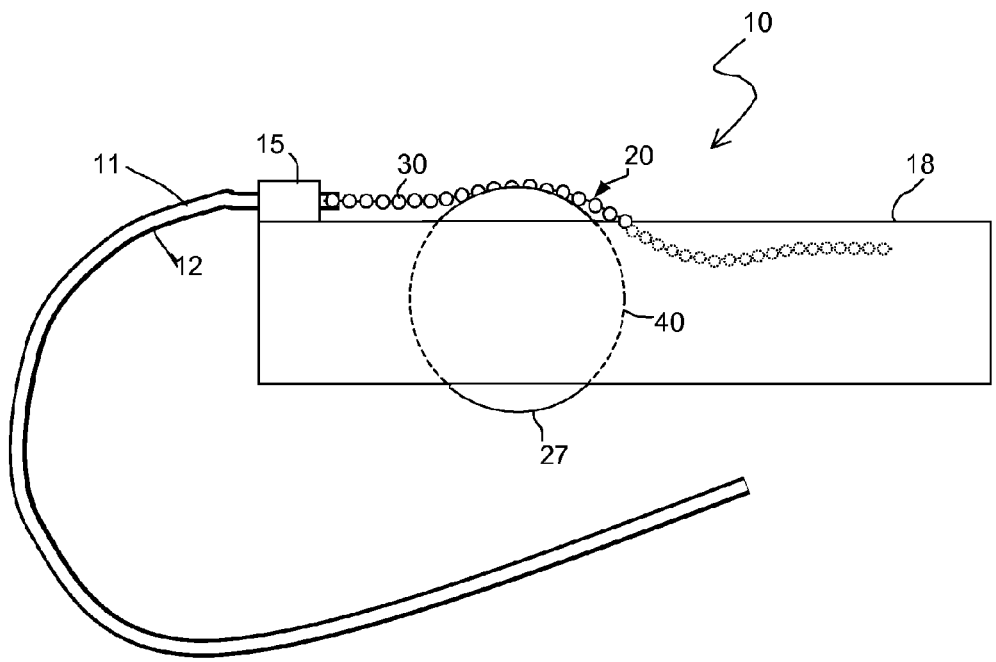
FIG. 5 is a side view of an alternative embodiment of the invention.

Piston member 20 is preferably of sufficient length that proximal end 24 thereof extends some distance beyond the proximal end of chamber 12. Thus, piston head 28 can be advanced and retracted within chamber 12 by advancing or retracting the proximal end 24 of piston member 20. In some embodiments proximal end 24 of piston member 20 may be received in handle 18 and may optionally be spooled, coiled, or otherwise stored therein. By way of example only, proximal end 24 may be spooled on a spool 50, as shown in phantom in FIG. 5. Tracks, guides, chambers and other suitable means for storing end 24 may also be used, if desired. In alternative embodiments, piston member 20 may not comprise a single continuous length of material and may instead comprise an assembly of members connected together so as to function as a piston member.

In order to facilitate movement of piston member 20, proximal end 24 of piston member 20 is, in some embodiments, provided with an engagement device 30. Engagement device 30 may take any of a variety of forms, but is preferably a feature that facilitates manual movement of piston member 20. In preferred embodiments, engagement device facilitates one-handed movement of piston member 20. Thus, in certain embodiments, engagement device 30 may comprise one or more bosses, grooves, ridges, bumps, bulges, or the like. In particular, the engagement devices or beads can be octagonal or any other shape that can engage the thumbwheel and any corresponding shape therein, if present. Rounded bead shapes are preferred for easier manufacturing and operation by users.

In the embodiment shown in FIGS. 2-4 and 6, piston member 20 comprises a length of beaded cable tie, with the result that the sequential beads along its length can function as engagement devices. In addition, the beads in this embodiment help to keep piston member centered within chamber 12.

Figure 4:
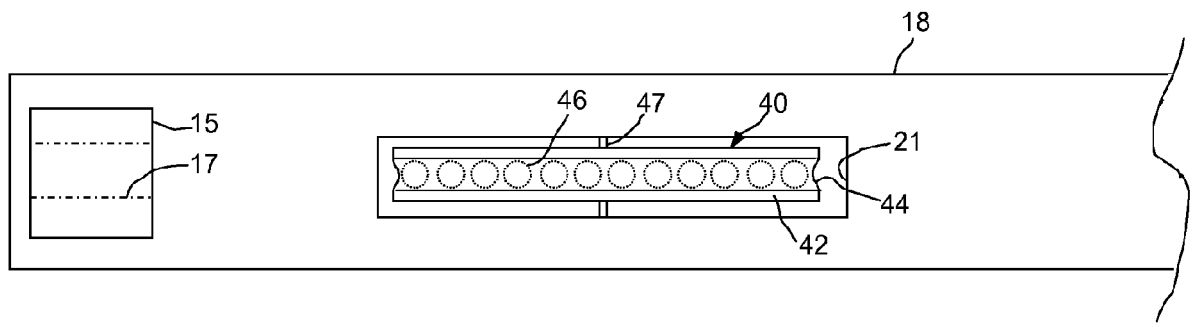
FIG. 4 is a top view of the handle of the embodiment of FIG. 2.

To further facilitate movement of piston member 20, some embodiments of the present device are provided with a thumbwheel 40 rotatably mounted in or on handle 18, as shown at 40 in FIGS. 2 and 4. Referring particularly to FIG. 4, in certain embodiments, thumbwheel 40 is mounted on an axle 47 within handle 18 and extends partially out of handle 18 through an opening 21. Thumbwheel 40 is preferably positioned such that its perimeter 42 is parallel to the general direction of piston member 20 where it is exits from chamber 12. In other embodiments, thumbwheel 40 may have a diameter that is greater than the depth of handle 18 and may be positioned such that it extends out of handle 18 through openings in both the top and bottom surfaces of handle 18, as shown at 27 in FIG. 5.

To facilitate engagement of piston member 20, edge 42 preferably includes a circumferential groove 44. An operator of the tool may, by capturing the proximal end 24 of piston member between his thumb and the edge of thumbwheel 40, readily advance or retract piston member 20, thereby advancing or retracting piston head 28 at the distal end of the tool.

In embodiments in which piston member 20 includes one or more engagement devices, thumbwheel 40 may include one or more complementary devices. Thus, for example, if piston member 20 comprises cable tie material, groove 44 may include one or more depressions 46 that are sized and spaced to receive successive beads. Alternatively, engagement devices may be provided on thumbwheel 40 and receiving devices on piston member 20, so that thumbwheel 40 engages piston member 20 in the manner of a gear engaging a chain. It will be understood that the nature and/or presence of engagement devices is not critical to the operability of the invention.

Figure 6:
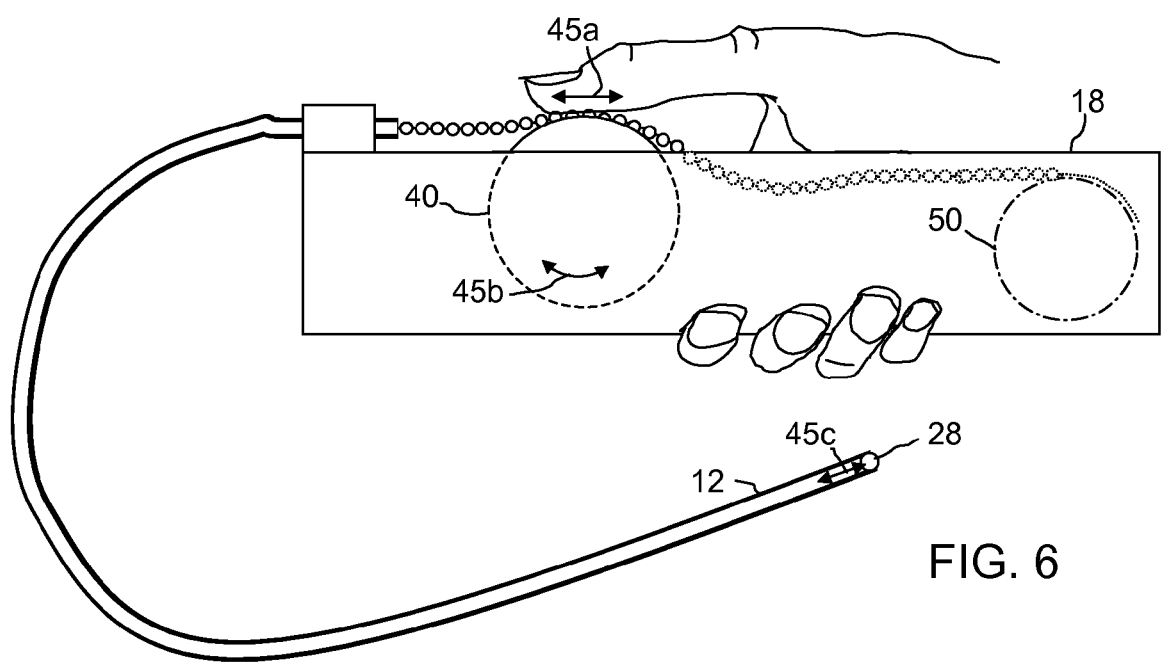
FIG. 6 is an illustration showing the embodiment of FIG. 2 in use.

Referring now to FIG. 6, when it is desired to remove a sample of oil from an oil reservoir, such as may occur in the course of routine engine maintenance tests, the present device is configured such that piston head 28 is at or near the oil inlet 13 of chamber 12. If piston head 28 is not positioned at or near inlet 13, operation of the tool will be sub-optimal. For example, if piston head 28 extends beyond inlet 13, fluid will enter chamber 12 behind piston head 28. Fluid behind piston head 28 may remain in the tool indefinitely or may be dispensed with one or more subsequent samples, causing contamination.

Chamber 12 is then positioned such that its oil inlet 13 is submerged in the oil that is to be sampled. Piston member 20 extends from piston head 28, through the length of chamber 20 and from the proximal end of chamber 20 toward handle 18. By aligning the proximal end of piston member 20 with thumbwheel 40 and moving his thumb, or thumb and forefinger in the embodiment shown in FIG. 5, as shown at arrow 45a, thereby rotating thumbwheel 40 as shown by arrow 45b, the operator can retract piston member 20 as shown at arrow 45c, thereby pulling piston head 28 into chamber 12 and drawing an oil sample into chamber 20 via inlet 13.

It may be preferred in some embodiments to provide a means for ensuring that the oil sample has a predetermined volume. This may be accomplished by providing one or marks, such as on piston member 20 and/or handle 18 and/or thumbwheel 40, or elsewhere. The position(s) of such mark (s) can be set and/or annotated so as to indicate when piston head 28 has been retracted sufficiently to have withdrawn a desired sample size. An exemplary sample size may be 2 ml. Alternatively, chamber 12 may be such that it is possible to view piston head 28 through the chamber wall, so that a visible determination of the position of piston head 28 may be made. Still further, a stop means may be provided, such as within chamber 12, on handle 18, on clip 15, or elsewhere. The stop means, if present, may prevent piston head 28 from being retracted beyond a desired point thereby preventing the withdrawal of overlarge samples. For example, a heat shrinkable collar may be added to a beaded piston member at the point where it is desired to position the stop means, so as to prevent the piston member from traveling further.

When it is desired to discharge the oil sample, such as into a testing device (not shown), the operator reverses the process and advances piston member 20 into chamber 12. Because piston head 28 preferably forms a fluid seal with the inside of chamber 12, substantially all of the oil within chamber 12 will be discharged if piston head 28 is extended all the way to oil inlet 13. If piston head 28 is not extended all the way to inlet 13, some fluid may remain in the chamber and may thus contaminate subsequent samples. It is therefore preferred in some embodiments to provide a means for ensuring complete dispensing of each sample. This may take the form of one or marks, such as on piston member 20 and/or handle 18 and/or thumbwheel 40, or elsewhere. The position(s) of such mark (s) can be set and/or annotated so as to indicate when piston head 28 is at inlet 13. Alternatively, chamber 12 may be such that it is possible to view piston head 28 through the chamber wall, so that a visible determination of the position of piston head 28 may be made. Still further, a stop means may be provided, such as at inlet 13, on handle 18, on clip 15, or elsewhere. The stop means, if present, may both prevent piston head 28 from exiting through inlet 13 and also be used to ensure complete dispensing of the fluid sample.

Because the present device comprises a flexible tube and a compact handle, it is much less cumbersome and therefore easier to carry and handle than previous devices. Because substantially all of each sample is discharged, successive samples are not contaminated and it is not necessary to clean the device between samples. The present device can be operated easily and repeatedly, without risk of damage to the device. In addition, the present device makes it possible to retrieve fluid samples from fluidic samples from reservoirs that are difficult to access, such as industrial rotational equipment.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. For example, the present device may be used to sample fluids other than oil, and from environments other than an engine.

It is to be understood that the forms of the invention shown and described herein may be taken as the presently preferred embodiments. Elements and materials may be substituted for those illustrated and described herein, parts and processes may be reversed, and certain features of the invention may be utilized independently, all as would be apparent to one skilled in the art after having the benefit of this description to the invention. Changes may be made in the elements described herein without departing from the scope of the invention as described in the following claims. In addition, it is to be understood that features described herein independently may, in certain embodiments, be combined.

What is claimed is:

1. A device for retrieving a fluid sample, comprising:
a chamber having an inside wall and at least one oil inlet;
a piston head received in said chamber and slidable between an empty position in which it is disposed substantially at said inlet and a filled position in which it is a first distance from said inlet;
a handle affixed to said chamber; and
a piston member extending between said handle and said piston head, characterized in that at least a portion of said chamber comprises a flexible tube and said piston member comprises a length of beaded cable tie having a proximal end and a distal end, said distal end being affixed to said piston head.

2. The device according to claim 1 wherein said handle includes a thumbwheel that engages said piston member such that rotation of said thumbwheel advances or retracts said piston-advancing mechanism.

3. The device according to claim 1 wherein said chamber consists of a length of flexible tubing.

4. The device according to claim 1 wherein said proximal end of said piston member includes at least one engagement device.

5. The device according to claim 1 wherein said handle includes a thumbwheel that engages said piston member such that rotation of said thumbwheel advances or retracts said piston-advancing mechanism and wherein said thumbwheel and said proximal end of said piston include complementary engaging devices.

6. The device according to claim 1 wherein said piston is adapted to move between an empty position in which said piston is at said oil inlet and a full position in which said piston is retracted from said oil inlet by a desired amount.

7. A system for assessing properties of oil in an engine, comprising:
the oil sampling device according to claim 1; and
an oil assessing device adapted to receive oil from said oil sampling device.

8. A method for assessing properties of oil in an engine, comprising:
providing a sampling tool according to claim 1;
using the sampling tool to withdraw an oil sample from the engine;
dispensing the oil sample from the sampling tool; and
assessing the properties of the oil sample.

* * * * *